United States Patent
Robb et al.

(10) Patent No.: US 9,422,551 B2
(45) Date of Patent: Aug. 23, 2016

(54) ADAPTERS FOR LIGATION TO RNA IN AN RNA LIBRARY WITH REDUCED BIAS

(71) Applicant: New England Biolabs, Inc., Ipswich, MA (US)

(72) Inventors: G. Brett Robb, Somerville, MA (US); Ryan T. Fuchs, Peabody, MA (US); Fanglei Zhuang, Peabody, MA (US)

(73) Assignee: New England Biolabs, Inc., Ipswich, MA (US)

( * ) Notice: Subject to any disclaimer, the term of this patent is extended or adjusted under 35 U.S.C. 154(b) by 69 days.

(21) Appl. No.: 13/904,452

(22) Filed: May 29, 2013

(65) Prior Publication Data

US 2014/0357528 A1   Dec. 4, 2014

(51) Int. Cl.
*C12Q 1/68* (2006.01)
*C12N 15/10* (2006.01)

(52) U.S. Cl.
CPC ............................ *C12N 15/1096* (2013.01)

(58) Field of Classification Search
None
See application file for complete search history.

(56) References Cited

U.S. PATENT DOCUMENTS

| | | | |
|---|---|---|---|
| 2007/0065844 A1* | 3/2007 | Golub | C12Q 1/6834 435/6.14 |
| 2010/0068711 A1* | 3/2010 | Umansky | C12Q 1/6806 435/6.16 |
| 2011/0104785 A1* | 5/2011 | Vaidyanathan | C12N 15/10 435/196 |
| 2012/0322691 A1* | 12/2012 | Sachidanandam et al. | 506/16 |
| 2013/0330778 A1* | 12/2013 | Zeiner | C12N 15/1096 435/91.21 |

FOREIGN PATENT DOCUMENTS

| | | | |
|---|---|---|---|
| WO | WO0240664 A1 | | 5/2002 |
| WO | WO2013017861 | * | 2/2013 |

OTHER PUBLICATIONS

Sorefan et al. Silence 3(1)(2011): 4-4.*
Zhuang et al. Nucleic acids research 40.7 (2012): 14 pages.*
Sorefan et al.Silence 3(1 )(2011): 4-4.*
GOLUB IDT (attached, IDT primer-dimer program, available at https://www.idtdna.com/calc/ analyzer, accessed Dec. 3, 2015).*
Meyer et al. (Targeted high-throughput sequencing of tagged nucleic acid samples, Nucleic Acids Res. 2007;35(15):e97. Epub Aug. 1, 2007).*
Hoeijmakers et al. (Linear amplification for deep sequencing, Nat Protoc. Jun. 23, 2011;6(7):1026-36. doi: 10.1038/nprot.2011.345).*
Broude et al. (Multiplex allele-specific target amplification based on PCR suppression, PNAS, Jan. 2, 2001, vol. 98, No. 1, pp. 206-211).*
Sun, et al., RNA, 17, 2256-2262 (2012).
Zhuang, et al., Nucleic Acids Res, 40, e54 (2012).
Sorefan, et al.,Science, 3, 4 (2012).
Jayaprakash, et al., Nucleic Acids Res, 39, e141 (2011).
Hafner, et al., RNA, 10.1261/rna.2799511 (2011).
Alon, et al., Genome Research, 21, 1506-1511 (2011).
Nishigaki, et al., Molecular Diversity, 4, 187-190 (1998).
Tang, et al., Nucleic Acids Research, 41, 3, e44 (2013).
Giardine, et al., Genome Research, 15, 1451-1455 (2005).
Goecks, et al., Genome Biology, 11:R86 (2010).
Blankenberg, et al., Current Protocols in Molecular Biology, Chapter 19, Unit 19.10.1-21 (2010).
Hafner, et al., Methods, 44, 3-12 (2008).
Berninger, et al., Methods, 44, 13-21 (2008).
Sternberg, et al., Mechanism of substrate selection by a highly specific Crispr endoribonuclease, RNA, 18:1-12, 2012.

* cited by examiner

*Primary Examiner* — Aaron Priest
(74) *Attorney, Agent, or Firm* — New England Biolabs, Inc.; Harriet M. Strimpel (57) ABSTRACT

An improved adapter design for ligation to target RNA in a library is described which enables target RNAs that would normally be under-represented or not represented at all in a cDNA library or a PCR product of the cDNA library, to be represented with average frequency.

17 Claims, 4 Drawing Sheets

ADAPTERS FOR LIGATION TO RNA IN AN RNA LIBRARY WITH REDUCED BIAS

BACKGROUND

High-throughput sequencing (HTS) is a powerful tool for the analysis of RNA molecules (Hafner, et al. *Methods*, 44:3-12 (2008); Berninger, et al. *Methods*, 44:13-21 (2008)). HTS allows the detection of single base differences between molecules, the discovery of undefined molecules and the determination of the differences in RNA composition or expression between different samples. For RNA analysis in HTS, sequencing libraries are typically constructed through a multistep process starting with the ligation of adapters to the ends of the RNA followed by reverse transcription (RT) into cDNA and amplified by PCR prior to HTS sequencing. However, bias has been detected in the ligation of adapters to the RNA that results in some members of an RNA library being misrepresented. This has implications for understanding the biological role of members of the library. For example, HTS experiments have misrepresented the quantity of some small RNAs in a mixture from 2 to 50 fold (Hafner, et al. *RNA*, 17:1697-1712 (2011) and Alon, et al. *Genome Research*, 21:1506-1511 (2011)). This type of bias can lead to failure to detect or accurately quantitate species of RNAs that has adverse consequences in understanding the biology of a cell or tissue.

SUMMARY

In general in one aspect, a preparation is provided that includes an RNA in a library of RNA molecules ligated to: (a) a 3' polynucleotide adapter having a 3' end and a 5' end wherein a first defined nucleotide sequence is located at the 5' end, the 3' polynucleotide adapter comprising a first random nucleotide sequence located between the 3' end and the first defined nucleotide sequence; and (b) a 5' polynucleotide adapter having a 5' end and a 3' end, wherein a second defined nucleotide sequence is located at the 3' end, the 5' polynucleotide adapter comprising a second random nucleotide sequence located between the 5' end and the second defined nucleotide sequence.

In general in one aspect, a preparation is provided that includes an RNA in a library of RNA molecules ligated to: (a) a 3' polynucleotide adapter comprising a first nucleotide sequence; and (b) a 5' polynucleotide adapter comprising a second nucleotide sequence; wherein the first nucleotide sequence is complementary to the second nucleotide sequence.

In general in one aspect, a preparation is provided that includes an RNA in a library of RNA molecules ligated to: (a) a 3' polynucleotide adapter having a 3' end and a 5' end and comprising a first defined nucleotide sequence located at the 5' end, a first random nucleotide sequence located between the 3' end and the first defined nucleotide sequence, and a third nucleotide sequence; and (b) a 5' polynucleotide adapter, the 5' adapter having a 3' end and a 5' end and comprising a second defined nucleotide sequence positioned at the 3' end; wherein the 5' polynucleotide adapter is capable of hybridizing to the third nucleotide sequence in the 3' adaptor.

In another aspect, a feature of the preparation includes the third nucleotide sequence corresponding to a portion of the first defined nucleotide sequence.

In another aspect, a feature of the preparation includes the third nucleotide sequence being capable of hybridizing to a portion of the second defined sequence.

In another aspect, a feature of the preparation includes the length of the random nucleotide sequence being in the range of 2 nucleotides to 50 nucleotides.

In another aspect, the 3' polynucleotide adapter further includes a barcode sequence.

In another aspect, the 3' polynucleotide adapter is a DNA oligonucleotide and the 5' polynucleotide adapter is an RNA oligonucleotide.

In general in one aspect, a preparation is provided that includes an RNA in a library of RNA molecules having a 3' end and a 5' end, wherein the RNA is ligated at the 3' end to a 3' polynucleotide adapter having a 3' end and a 5' end, the 3' adapter having a nucleotide sequence that includes a first defined nucleotide sequence located at the 5' end; a first random nucleotide sequence located between the 3' end and the defined nucleotide sequence; and a third nucleotide sequence hybridized to a complementary nucleotide sequence on a 5' polynucleotide adapter.

In another aspect, the 3' polynucleotide adapter is DNA and the 5' polynucleotide adapter is RNA.

In another aspect, the third nucleotide sequence corresponds to a portion of the first defined sequence and the complementary nucleotide sequence on the 5' adapter corresponds to a portion of the second defined nucleotide sequence wherein the portion may be some or all of the first or second defined sequence.

In general in one aspect, a method is provided of making an RNA library suitable for PCR amplification is provided that includes (a) forming a preparation of the type described above; (b) reverse transcribing the RNA ligated to the adapters; and (c) amplifying the product of (b).

In one aspect, the method further includes ligating the 3' end of the 5' RNA oligonucleotide adapter to the phosphorylated 3' end of the target RNA.

In general in one aspect, a method is provided of ligating adapters to target RNA having 3' and 5' ends in an RNA library, that includes (a) obtaining (i) a 3' adenylated DNA adapter having a 3' and a 5' end and comprising a first random nucleotide sequence located adjacent to a first defined nucleotide sequence at the 5' end; and (ii) a 5' RNA oligonucleotide adapter having a 3' and a 5' end and comprising a second random nucleotide sequence located adjacent to a second defined nucleotide sequence at the 3' end; (b) ligating the 3' adenylated DNA adapter to an RNA in an RNA library; (c) allowing a portion of the 5' RNA adapter to hybridize to a portion of the 3' adenylated DNA adapter; and (d) ligating the hybridized 5' end RNA adapter to the RNA.

BRIEF DESCRIPTION OF THE FIGURES

FIG. 1A-E shows schematics of a standard library construction and FIG. 1F-J shows schematics of a structured adapter library construction.

FIGS. 2A and 2B show the effect on increase in efficiency of ligation on individual target RNAs using a complementary adapter design where the selected target RNAs are underrepresented or difficult to detect when the test library described in Example 2 is sequenced.

FIG. 3 shows the effect on bias reduction in library construction and analysis by high throughput sequencing. "MidRand" denotes location of a random nucleotide sequence distant from the ligation site with the target RNA. "MidRand C3" denotes a region complementary to the 3' adapter and adjacent to the ligation site with the target RNA where the random nucleotide sequence is adjacent to the complementary sequence but located at the opposite end relative to the ligation junction. "Std" denotes standard adapter. The percent of input miRNA pool members that were quantified as being less than 2-fold from the expected value was increased from 30% to 53% which corresponds to an increase of 77% when MidRand and MidRand C3 adapters were used. The percent of input miRNA pool members that were quantified as being greater than 10-fold different from the expected value was decreased from 19% to 4.2%, reflecting a decrease of 78%.

DETAILED DESCRIPTION

Reduced bias in adapter ligation to target RNA has been achieved using the compositions and methods described herein. Additional advantages include increased efficiency of ligation and ease of determination of where the adapter sequence ends and the target RNA sequence begins once the adapters are ligated to the target RNA and the target RNA is reversed transcribed, amplified and sequenced. In addition to the adapter design shown in FIGS. 1F and 1H it is possible to incorporate primer binding sites and/or barcode sequences in the oligonucleotide adapter sequence design. In an embodiment, the random nucleotide sequence serves as a barcode for the ligated target RNA.

The target RNA may be of any size and may be synthetic or naturally occurring.

In embodiments of the invention, the target RNA may be any of: a small RNA such as a micro RNAs (miRNA), piwi interacting RNA (piRNA), small interfering RNA (siRNA), repeat associated siRNA (rasiRNA), trans-acting siRNA (tasiRNA), CRISPR RNA (crRNA) transfer RNA (tRNA), Promoter-associated RNA (PASR), Transcription stop site associated RNAs, signal recognition particle RNA, transfer-messenger RNA (tmRNA), small nuclear RNA (snRNA), small nucleolar RNA (snoRNA), SmyRNA, small Cajal Body-specific RNA (scaRNA), Guide RNA (gRNA), Spliced leader RNA, Telomerase RNA, Ribonuclease P, or a large RNA such as long non-coding RNAs or messenger RNAs, retrotransposons, satellite RNA, virioids, viral genomes or fragments thereof.

The target RNA may be members of an RNA library, RNA pool, circulating, or environmental RNAs or populations of similar or identical RNAs; or an extract from an individual organism, tissue, cell, virus, or microvesicle.

The 3' and 5' adapters are individually formed from single stranded DNA or RNA polynucleotides, where one or both adapters are RNA, DNA or chimeric DNA and RNA, for example, the 3' adapter may be a single stranded DNA and the 5' adapter may be a single stranded RNA. The 3' adapter is so named because the 5' end ligates to the 3' end of the target RNA while the 5' adapter is so named because the 3' end ligates to the 5' end of target RNA. The adapters may be the same or different lengths to each other and of any desired length and when ligated to RNA can provide primer binding sites for downstream amplification, barcodes for source identification and/or tags for sorting into subpopulations. Their sequences and lengths may assume various secondary structures including loops and stems. It is generally more cost effective to synthesize adapters of a length of less than 100 nucleotides, for example less than 75 nucleotides, for example less than 50 nucleotides, for example less than 40 nucleotides, for example, less than 30 nucleotides. In an embodiment, the 3' and 5' adapters contain random sequences.

"Random" sequences generally refer to regions of sequence at which any nucleotide can occur. For instance, in a chemically synthesized oligonucleotide, a specific position in the oligonucleotide polymer could be specified to have any nucleotide incorporated. This is achieved introducing a mixture of nucleotides (most often dA, dG, dC, dT for DNA oligonucleotides, and dA, dG, dC and dU for RNA oligonucleotides) during the stepwise chemical reactions that result in oligonucleotide chain elongation.

"Defined" sequences in oligonucleotides refer to at least one unique nucleotide incorporated at a specific position within the oligonucleotide. During the stepwise chemical reactions that result in oligonucleotide chain elongation, one or more nucleotides are introduced to a specific nucleotide sequence at a specific position.

"Portion" refers to some or all of a defined region or sequence which may be contiguous or non-contiguous.

The 3' and 5' adapters may have a complementary region. The complementary region means a sequence on the 3' adapter that is complementary to a sequence on the 5' adapter. The complementary region should be at least 5 nucleotides or 7 nucleotides or 8 nucleotides or can be as long as the entire length of the adapter. The complementary region may be contiguous or non-contiguous providing that hybridization can occur between the two adapters under suitable hybridization conditions. The complementary sequence should be of sufficient length to hybridize to its counterpart and may additionally serve to delineate the boundaries of the target RNA. In the latter case, the complementary sequence may correspond to a portion of the defined sequence at the 3' end of the 3' adapter or the 5' end of the 5' adaptor. Alternatively, the complementary sequence may correspond to non-random region in a location in the adaptor that overlaps or is separate from the end defined sequences.

The 3' and 5' adapters may comprise random sequences located at a position that is not adjacent to the ligation site where at least 5 non-random nucleotides are positioned between the ligation site and the random sequences. Alternatively, the random nucleotide sequence may be as short as 3 nucleotides or any length in between 3 nucleotides and the entire length of the adapter except for at least 5 non-random nucleotides. Methods for generating a random sequence are provided in the examples (see Example 2).

The 3' and 5' adapters may include nucleotide modifications including at their ends or within their sequence that could include; affinity tags such as biotin, fluorescent molecules such as fluorescein or cyanine, nucleotides with modified bases, nucleotides with modified sugars, or other modifications designed to introduce various functionalities.

In an embodiment, the adapters include both a random nucleotide sequence and a complementary sequence. In another embodiment, random sequences are optional. A primer binding site and a bar code may optionally be included in one or both adapters.

The design of the 3' adapter may be different from that of the 5' adapter varying for example in length and sequence except that a complementary sequence between the two adapters may be present. In the examples, adapters of 21 nucleotides (3' adapters) and 26 nucleotides (5' adapters) were used but these lengths are not intended to be limiting. Where primer binding sites are desired in the adapter sequence, these may be located at any position in the adapter other than the position of the random nucleotide sequence.

Ligation of the DNA and RNA adapters to the target RNA can be achieved using a suitable nucleic acid ligase such as T4 RNA ligase 1 (T4 Rnl1) T4 RNA ligase 2 (T4 Rnl2), T4 RNA ligase 2 truncated (also defined as T4 RNA Ligase 2 1-249) and T4 ligase 2 truncated K227Q (T4 Rnl2tr K227Q), T4 DNA ligase 2 truncated R55K, K227Q (T4 Rnl2tr KQ), T4 DNA ligase, T3 DNA ligase, T7 DNA ligase, *E. coli* DNA ligase, 9° N™ DNA ligase, *Thermus aquaticus* DNA ligase, *Paramecium bursaria chlorella* virus 1 (PBCV-1) ligase, *Methanobacterium thermoautotrophicum* RNA ligase (Mth ligase), or RtcB family ligases such as *E. coli* RtcB ligase or variants of these ligases (New England Biolabs, Ipswich, Mass.) that support the complete ligation reaction or at least phosphodiester bond formation between nucleic acid polymers. Using adapters of the type described above, it was possible to achieve greater than 60% for example 65%, for example 70% increase efficiency of ligation for the population as a whole compared with the same target RNAs to which adapters lacking both complementary regions were ligated.

Using adapters of the type described above, it was possible to achieve greater than 60% for example 65%, for example 70% increase in ligation efficiency compared with the same target RNAs to which adapters lacking complementary regions were ligated.

Using adapters of the type described above, it was possible to achieve a decrease of at least 60% for example 65%, for example 70% for example 75% decrease in bias compared with the same pool of target RNAs to which adapters lacking both random nucleotides and complementary regions were ligated. Reduction of bias is indicated by % increase in RNA pool members whose quantities are measured by RNA sequencing to be less than 2-fold difference from expected. Reduction of bias is also indicated by the % decrease of RNA pool members whose quantities are measured by RNA sequencing to be greater than 10-fold different from expected when comparing sequencing libraries constructed using adapters of the type described above as compared to standard adapters.

As shown in FIG. 1A-J, the ligation of adapter to target RNA is intended to facilitate downstream reactions. In an embodiment, RT generates a cDNA from the adapter ligated RNA and this cDNA can then be amplified either by isothermal amplification techniques or temperature cycling techniques. Whereas FIG. 1D-E, I-J shows RT and amplification as two separate steps, they may be completed in a single step. These reactions may include the use of a single polymerase (for example, having reverse transcriptase activity in addition to polymerase activity such as commercially available (New England Biolabs, Ipswich, Mass.)). The amplified DNA may then be sequenced in a commercial sequencing instrument.

Figure 2:
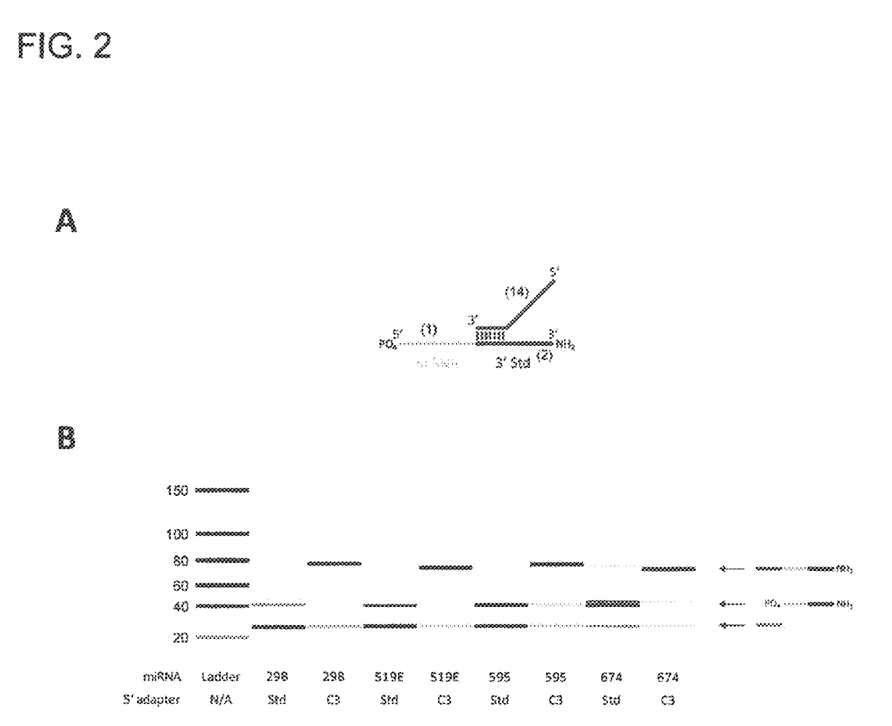
FIG. 2A is a cartoon showing the hybridization of an 5' RNA adapter to a 3' DNA adapter at a complementary region (C3=an adapter with a complementary region (15), Std=standard adapter sequence). The 3' DNA adapter (2) is shown ligated to RNA (1).
FIG. 2B shows the results of ligation experiments obtained with four substrates (std=standard 5' RNA adapter, C3=5b' RNA adapter with a complementary sequence to that in the 3' DNA adapter where 29B, 519E, 595 and 674 are individual target RNAs.

Increased efficiency in ligation of target RNAs selected for their normally inefficient ligation to standard adapters were shown using the improved adapters described herein as described in Example 1 and shown in FIG. 2B. The data showed an increase of at least 10 fold in ligation efficiency compared to standard adapters. This suggested that use of the improved adapters would reduce bias of similar target RNAs in a library of target RNAs. This was confirmed to be the case using HTS of the amplified DNA products of each target RNA in a library of target RNAs containing 962 different miRNAs in approximately equal concentration. The results showed significant reduction in bias in the ligated libraries (see for example, Example 2 and FIG. 3).

The ability to obtain sequence data for an accurately represented population of target RNAs in which ligation bias has been reduced is important for a number of applications. These include (a) quantification of transcription products in transcript expression profiling (b) transcript discovery in which maturation and biosynthesis intermediates can be detected and analyzed (such as for miRNAs which can be post transcriptionally modified by cleavage, trimming and addition of sequences); and (c) transcript geography where the role of localization can be determined.

All references cited herein are incorporated by reference.

EXAMPLES

Example 1

5'-RNA Adapter Ligation of Small RNAs

Ligation Reactions

Figure 1:
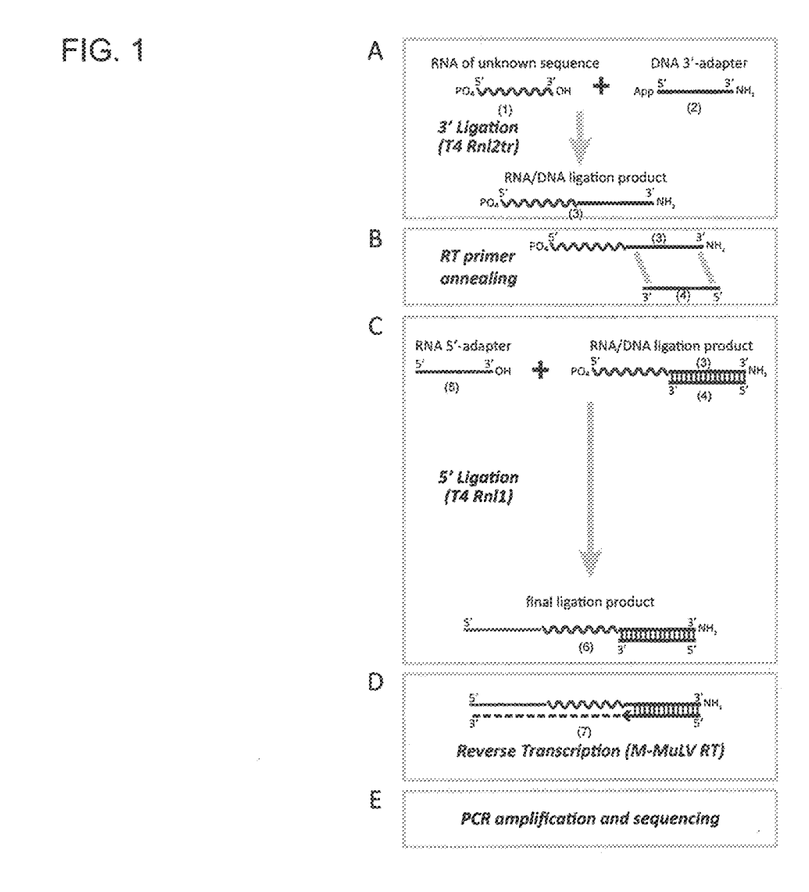
FIG. 1A shows the ligation of an RNA of undefined sequence (1) to a DNA adapter (2) resulting in a ligation product (RNA/DNA ligation product) (3).
FIG. 1B shows the annealing of a RT primer (4) and RNA/DNA ligation product (3).
FIG. 1C shows the ligation of (3) to an RNA adapter (5) to form a final ligation product consisting of the target RNA ligated to a DNA adapter at the 3' end and an RNA adapter at the 5' end (6).
FIG. 1D shows RT of the target RNA using a reverse transcriptase to generate a cDNA (7).
FIG. 1E corresponds to the PCR amplification and sequencing step.
FIG. 1F shows a target RNA (1) and a DNA adapter (8) having a randomized sequence in the mid region of the 3' adapter (3' MidRand adapter) which allows for the formation of secondary structure between the RNA and the adapter that is favorable for ligation. The RNA/DNA ligation product is shown with the randomized sequence shown as a jagged line (9) adjacent to a sequence that is complementary to a sequence on an RNA adapter shown as a heavy blackline.
FIG. 1G shows the annealing of a RT primer (11) to the RNA/DNA ligation product (9).
FIG. 1H shows an RNA adapter (10) (5' MidRand C3) with a randomized nucleotide sequence (shown as a jagged line) and a sequence (shown as a heavy grey line) complementary to (8). Ligation occurs between the target RNA and the 3' end of the RNA adapter (10) to produce the final ligation product (12). A primer (11) may anneal to the 3' end or the 3' adapter.
FIG. 1I shows RT of the target RNA using a reverse transcriptase to generate a cDNA (13).
FIG. 1J corresponds to the PCR amplification and sequencing step.

The ligation efficiency of defined sequence RNA adapters to the 5'-end of defined substrates was determined as described below. Mixed RNA/DNA oligos were purchased from Integrated DNA Technologies (IDT®, Coralville, Iowa) that correspond to a miRNA sequence on the 5' half of the oligo and the DNA sequence of a 3' Std adapter on the 3' half of the oligo (sequences are detailed in Table 1). Each ligation experiment contained one of these oligos (5 µM), a 5' adapter (10 µM), 20 units of murine RNase Inhibitor, (New England Biolabs, Ipswich, Mass.), and 10 units of T4 Rnl1 in a buffer (31 mM Tris-HCl pH 7.5, 6.3 mM $MgCl_2$, 0.63 mM DTT, 0.2 mM ATP, 5.2% PEG8000). The ligation reaction was incubated at 25° C. for 1 hour and then the products of the reaction were analyzed on an Agilent 2100 Bioanalyzer (Agilent Technologies, Santa Clara, Calif.) using an Agilent Small RNA Kit (Agilent Technologies, Santa Clara, Calif.).

miRNA Ligation Efficiency of Selected Individual RNAs is Improved with 5' Adapters that are Complementary to the 3' Adapters Four miRNA sequences were chosen because of the negative bias in adapter ligation reactions for these sequences using standard adapters. The miRNAs were miR-29B, miR-519E, miR-595, miR-674; (FIG. 2B). These were subjected to a 5' ligation reaction with either the 5' Std adapter or to a 5' C3 adapter specifically designed such that the last 7 bases on the 3'-end were complementary to the first 7 bases on the 5'-end of the 3' Std adapter (Table 1). The miRNA oligos used in the 5' ligation had the 3' Std adapter sequence (DNA) included in order to mimic the molecule that would be produced after 3' adapter ligation in a typical RNA library construction workflow (FIG. 1A and FIG. 2A). As shown in FIG. 2B, after 1 hour at 25° C. in the presence of T4 Rnl1 and ATP, the 4 miRNAs have virtually no detectable ligation product with the 5' Std adapter, but are all efficiently ligated to the 5' C3 adapters.

Example 2

HTS Library Preparation Using an Equimolar Pool of 962 Small RNA Oligonucleotides Oligonucleotides, Library Preparation and Sequencing The method is summarized in FIG. 1A-E for standard adapters and FIG. 1F-J for adapters with the characteristics described in the compositions detailed above.

The RNA input that was tested for the determination of reduction of bias was a commercially available pool of 962 miRNA oligonucleotides (miRXplore™ Universal Reference, Miltenyi Biotec Inc., Auburn, Calif.). The adapters were synthesized by IDT.

Adapters were synthesized using standard chemical methods that are widely accessible via service providing companies, for example: IDT, Life Technologies (Carlsbad, Calif.), etc. In the current state of the art workflow for chemical DNA or RNA oligonucleotide synthesis, regions of defined sequence were polymerized beginning at the 3' terminal nucleotide with chain elongation progressing in a 3'-5' direction. Sequential introduction of chemical building blocks that react to form the specifically desired nucleotide polymer sequence comprising dA, dC, dT, dG for DNA and comprising A, C, G, U for RNA was performed. This achieved the stepwise addition of nucleotide residues to the 5'-terminus of the growing chain, and the addition of one nucleotide can be considered one cycle. For positions of randomized sequence within a chemically synthesized oligonucleotide, a mixture of building blocks comprising dA, dC, dT, dG for DNA and comprising A, C, G, U for RNA is added in each cycle corresponding to the position in the desired oligonucleotide sequence. For example to synthesize the sequence 5'-GAGNNNUCU-3', the cycles of addition after the 3'-terminal U would be C, U, mixture of ACGU, mixture of ACGU, mixture of ACGU, G, A, G.

3' DNA adapters were adenylated using a 5'-DNA Adenylation Kit (New England Biolabs, Ipswich, Mass.). Adenylated adapters were gel purified on 20% Tris-borate-EDTA (TBE)-urea acrylamide gels before use.

Library preparation for high through put sequencing was carried out using a protocol based on NEBNext® Small RNA Library Prep Set for Illumine (Multiplex Compatible) (New England Biolabs, Ipswich, Mass.). All steps contained between 20 to 40 units of murine RNase Inhibitor (New England Biolabs, Ipswich, Mass.) except for the PCR step.

miRXplore™ Universal Reference RNA (~8 pmoles) were treated with 10 U of calf intestinal alkaline phosphatase (CIP; NEB) at 37° C. for 1 hour. The RNA was extracted with TR1 reagent (Life Technologies) and precipitated with isopropanol. The RNA was suspended to a concentration of 0.4 µM in a buffer (50 mM Tris-HCl pH 7.5, 10 mM MgCl2, 1 mM DTT, 12.5% PEG8000).

The 3'-ends of the RNAs were subjected to a ligation reaction with a pre-adenylated DNA adapter (1 µM) and 200 units of Ligase (T4 Rnl2tr KQ) for 1 hour at 25° C. Adapters used were 3' Std adapter, or 3' MidRand adapter (Table 1). 333 µM ATP and 10 units of T4 Polynucleotide Kinase (T4 PNK) (New England Biolabs, Ipswich, Mass.) were added and the sample was incubated at 37° C. for 30 minutes followed by 75° C. for 5 minutes to phosphorylate the 5'-end of the RNAs and heat inactivate the T4 PNK. This step is depicted schematically in FIGS. 1A, and 1F.

An oligonucleotide primer (RT primer for Std, or RT primer for MidRand; Table 1) for RT was added (1.2 µM) and annealed by heating to 75° C. for 5 minutes, 37° C. for 10 minutes, and 25° C. for 10 minutes (see WO 2012/033687 for method of reducing adapter dimer formation). This step is depicted schematically in FIGS. 1B and 1G.

A 5' RNA adapter (0.83 µM) and 18 units of T4 Rnl1 were then added to the RNAs and incubated at 25° C. for 1 hour. 5'-RNA adapters were 5' Std adapter or 5' MidRand C3 adapter (Table 1). This step is depicted schematically in FIGS. 1C and 1H.

The RT reaction (using 450 units of M-MuLV reverse transcriptase (New England Biolabs, Ipswich, Mass.), dNTPs (500 µM each), 1×M-MuLV RT buffer (New England Biolabs, Ipswich, Mass.), and 40% of the final ligation product) was incubated at 20° C. for 5 minutes, 25° C. for 10 minutes, 42° C. for 30 minutes, and 85° C. for 5 minutes (see FIGS. 1D and 1I).

10% of the cDNA library resulting from the RT reaction was amplified by 12 cycles of PCR using LongAmp® Taq 2× Master Mix (New England Biolabs, Ipswich, Mass.) and primers that included flanking sequences needed for analysis by HTS (sequences are shown in Table 1).

PCR products were gel purified on 6% acrylamide gels, eluted, recovered by ethanol precipitation, and then analyzed on an Agilent 2100 Bioanalyzer using an Agilent DNA 1000 Kit (Agilent Technologies, Santa Clara, Calif.). The resulting purified libraries were sequenced on the Ion PGM™ sequencer using Ion 316™ chips and the Ion OneTouch™ (Life Technologies, Carlsbad, Calif.) for bead templating.

Sequencing reads from the Ion PGM runs were imported into Galaxy (Giardine, et al. *Genome Research,* 15:1451-1455 (2005); Goecks, et al. *Genome Biology,* 11:R86 (2010); Blankenberg, et al. *Current Protocols in Molecular Biology*, Chapter 19, Unit 19.10.1-21 (2010)) (http://galaxyproject.org/) where tools were used to only retain reads from 60 to 75 bases in length and then to remove the adapter sequences. Sequences from experiments involving the miRXplore Universal Reference were annotated in Genomics Workbench 5.1 (CLC bio, Cambridge, Mass.) by using a reference file containing the 962 sequences found in the Universal Reference with a zero mismatch tolerance. The total number of annotated reads in each library was divided by 962 and that value is the expected number of reads that should have been obtained given each miRNA was in equal abundance in the Universal Reference. The number of reads for each miRNA was divided by this expected value as a normalization step so that results from different sequencing runs could be easily compared.

Adapters with Internal Regions of Randomized Sequence and that Form Regions of Complementary to Each Other Adjacent to Ligation Junctions Reduce Bias in Small RNA Sequencing Results In this example, a 3' DNA adapter with a 6 nt randomized region located 3' of the sequence 5'-dTCGTATG-3' (3'-MidRand adapter, Table 1) and a 5' RNA adapter with an internal 6 nt randomized region followed by the sequence 5'-CAUACGA-3' at the 3'-end (5' MidRand C3 adapter) were obtained by oligonucleotide synthesis. These adapters were used to produce sequencing libraries using miRXplore Universal Reference pool of 962 miRNA sequences as input material, in parallel with standard 5' and 3' adapters (3' Std adapter and 5' Std adapter, Table 1), according to the method described above and as outlined in FIG. 1A-J.

Figure 3:
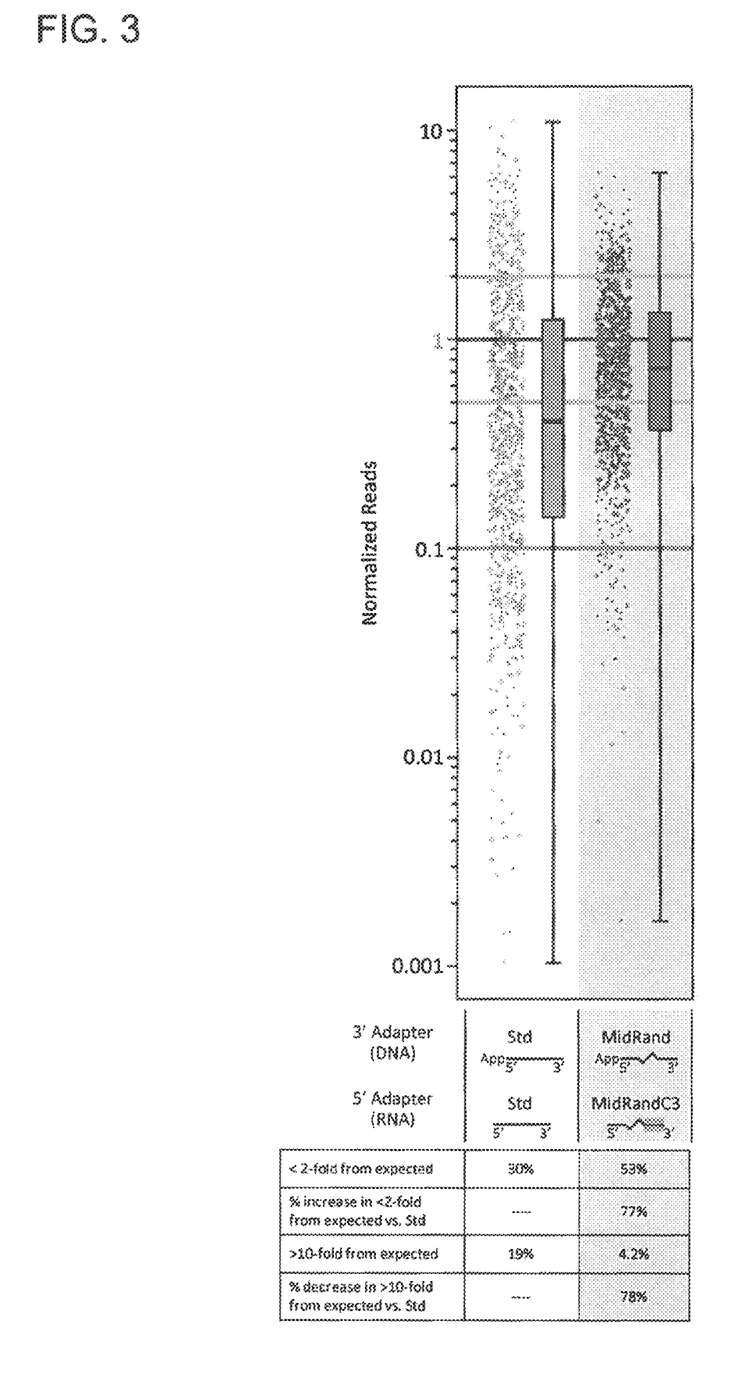

The libraries were sequenced on the Ion PGM. The sequencing reads were annotated with a zero mismatch tolerance, counted, normalized as described above such that each miRNA was expected to have a normalized read value of '1'. The individual normalized values for each miRNA were determined, and the data are plotted as individual data points corresponding to normalized values for each miRNA, and in a boxplot format in FIG. 3. Quantitative analysis of the data sets is shown in FIG. 3. The results showed that using an adapter containing randomized regions and regions that are complementary to each other adjacent to the ligation junctions results in a marked improvement in the sequencing results as indicated by more miRNAs being closer to their expected abundance and a tighter distribution of abundance values.

FIG. 3 compares quantitation from sequencing results for the library constructed using the 3' MidRand adapter and 5' MidRand C3 adapter to that of the library constructed using 3' Std adapter and 5' Std adapter. The percent of input miRNA pool members that were quantified as being less that 2-fold from the expected value was increased from 30% to 53% which corresponds to an increase of 77%. The percent of input miRNA pool members that were quantified as being greater than 10-fold different from the expected value was decreased from 19% to 4.2%, reflecting a decrease of 78%. It is clear from the data in FIG. 3 that performing library construction with the 3' MidRand+5' MidRand C3 adapters instead of 3' Std and 5' Std adapters produces HTS results that are a much better reflection of the initial miRNA population.

TABLE 1

List of sample adapter sequences to illustrate the general concept described in FIG. 1A-C, F-H.

| Items in FIG. | Oligonucleotide Name | Type | # of bases | 5'-end | 3'-end | Sequence |
|---|---|---|---|---|---|---|
| (2) | 3' Std adapter | DNA | 21 | App | $NH_2$ | TCGTATGCCGTCTTCTGCTTG (SEQ ID NO: 1) |
| (8) | 3' MidRand adapter | DNA | 21 | App | $NH_2$ | TCGTATGNNNNNNTCTGCTTG (SEQ ID NO: 2) |
| (5) | 5' Std adapter | RNA | 26 | OH | OH | GUUCAGAGUUCUACAGUCCG ACGAUC (SEQ ID NO: 3) |
| (14) | 5' C3 adapter | RNA | 26 | OH | OH | GUUCAGAGUUCUACAGUCCC AUACGA (SEQ ID NO: 4) |
| (10) | 5' MidRand C3 adapter | RNA | 32 | OH | OH | GUUCAGAGUUCUACAGUCCN NNNNNCAUACGA (SEQ ID NO: 5) |
| (4) | RT primer for Std | DNA | 21 | OH | OH | CAAGCAGAAGACGGCATACGA (SEQ ID NO: 6) |
| (11) | RT primer for MidRand | DNA | 31 | OH | OH | CCTCTCTATGGGCAGTCGGTG ATCAAGCAGA (SEQ ID NO: 7) |
|  | PCR primer 1 | DNA | 49 | OH | OH | CCATCTCATCCCTGCGTGTCT CCGACTCAGGTTCAGAGTTCT ACAGTCC (SEQ ID NO: 8) |
|  | PCR primer 2 | DNA | 17 | OH | OH | CCTCTCTATGGGCAGTC (SEQ ID NO: 9) |
| (1 + 2) | miR-29B + 3' Std | RNA/DNA | 44 | $PO_4$ | $NH_2$ | UAGCACCAUUUGAAAUCAGU GUU/TCGTATGCCGTCTTCTGCTTG (SEQ ID NO: 10) |
| (1 + 2) | miR-519E + 3' Std | RNA/DNA | 43 | $PO_4$ | $NH_2$ | AAGUGCCUCCUUUUAGAGUG UU/TCGTATGCCGTCTTCTGCTTG (SEQ ID NO: 11) |
| (1 + 2) | miR-674 + 3' Std | RNA/DNA | 43 | $PO_4$ | $NH_2$ | GCACUGAGAUGGGAGUGGU GUA/TCGTATGCCGTCTTCTGCTTG (SEQ ID NO: 12) |
| (1 + 2) | miR-595 + 3' Std | RNA/DNA | 42 | $PO_4$ | $NH_2$ | GAAGUGUGCCGUGGUGUGU CU/TCGTATGCCGTCTTCTGCTTG (SEQ ID NO: 13) |

The invention claimed is:

1. A set of reagents for producing adaptor-ligated RNA, comprising:
   (a) a population of 3' polynucleotide adaptors each having a 3' end and a 5' end,
   wherein each adaptor comprises:
      (i) a first non-random sequence of at least seven defined nucleotides at the 5' end,
      (ii) a first random nucleotide sequence located between the 3' end and the first defined nucleotide sequence,
      (iii) a third non-random sequence of at least 5 defined nucleotides, and
      (iv) a modified nucleotide at the 3' end,
      and wherein the first random nucleotide sequence varies in the population of 3' polynucleotide adaptors;
   (b) a 5' polynucleotide adapter, the 5' adapter having a 3' end and a 5' end and comprising a second non-random sequence of at least seven contiguous nucleotides that is complementary to the first non-random sequence of (a)(i); and
   (c) a ligase capable of ligating RNA.

2. The set of reagents according to claim 1, wherein the length of the first random nucleotide sequence is in the range of 2 nucleotides to 50 nucleotides.

3. The set of reagents according to claim 1, wherein the 3' polynucleotide adapter further comprises a barcode sequence.

4. The set of reagents according to claim 1, wherein the 3' polynucleotide adaptor is a DNA oligonucleotide and the 5' polynucleotide adapter is an RNA oligonucleotide.

5. A method of ligating adapters to target RNA having 3' and 5' ends in an RNA library, comprising:
   obtaining the set of reagents of claim 1;
   ligating the 3' adapter to an RNA in an RNA library;
   allowing a portion of the 5' adapter to hybridize with a portion of the sequence of the 3' adapter; and
   ligating the hybridized 5' end RNA adapter to the RNA.

6. The set of reagents of claim 1, wherein:
   (a) the 3' adapter comprises, from 5' to 3': the first non-random sequence, the first random nucleotide sequence, and the third non-random sequence; and
   (b) the 5' adaptor comprises a second random nucleotide sequence that is 5' to the second non-random sequence of (b).

7. The set of reagents of claim 6, wherein the first and second random nucleotide sequences are independently in the range of 2 to 50 nucleotides in length.

8. The set of reagents of claim 6, wherein the 3' adapter is 5' adenylated.

9. The set of reagents of claim 6, wherein the 5' adaptor comprises a 5' hydroxyl.

10. The set of reagents of claim 6, wherein the 3' and 5' adaptors are both DNA oligonucleotides.

11. A set of reagents according to claim 1, wherein the wherein the 3' and 5' adaptors are both RNA oligonucleotides.

12. The set of reagents of claim 6, wherein the ligase is a T4 RNA ligase.

13. A set of reagents, comprising:
   (a) a population of 3' polynucleotide adaptors each having a 3' end and a 5' end wherein each adapter, comprises:
      (i) a first non-random sequence of at least seven defined nucleotides at the 5' end,
      (ii) a first random nucleotide sequence located between the 3' end and the first defined nucleotide sequence, wherein each of the first random sequences in the population of 3' adapters comprises a different sequence
      (iii) a third non-random sequence of at least 5 defined nucleotides, and
      (iv) a modified nucleotide at the 3' end, and wherein the first random nucleotide sequence varies in the population of 3' polynucleotide adaptors;
   (b) a 5' polynucleotide adapter, the 5' adapter having a 3' end and a 5' end and comprising a second non-random sequence of at least seven contiguous nucleotides that is complementary to the first non-random sequence of (a)(i);
   (c) a ligase capable of ligating RNA;
   (d) a reverse transcription primer comprising a 3' end that is complementary with and hybridizes to the third non-random sequence of (a)(iii); and
   (e) a reverse transcriptase.

14. The set of reagents of claim 6, wherein the 3' adapter further comprises a barcode.

15. The set of reagents of claim 6, further comprising a reverse transcriptase.

16. The set of reagents of claim 6, wherein the 5' and 3' adaptors contain a primer binding site in the first or second defined nucleotide sequence or in a third or fourth defined nucleotide sequence.

17. A method of ligating adapters to target RNA having 3' and 5' ends in an RNA pool, comprising:
   obtaining the set of reagents of claim 6;
   ligating the 3' adapter to an RNA in a pool of RNA;
   allowing the 3' end of the 5' adapter to hybridize with the 5' end of the 3' adapter; and
   ligating the hybridized 3' end of the 5' adapter to the RNA.

* * * * *

SEQUENCE LISTING

<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
tcgtatgccg tcttctgctt g                                          21

<210> SEQ ID NO 2
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(13)
<223> OTHER INFORMATION: n is a, c, g, or t

<400> SEQUENCE: 2
tcgtatgnnn nnntctgctt g                                          21

<210> SEQ ID NO 3
<211> LENGTH: 26
<212> TYPE: RNA
<213> ORGANISM: Artificial Sequence
<220> FEATURE:
<223> OTHER INFORMATION: Synthetic construct

<400> SEQUENCE: 3
guucagaguu cuacaguccg acgauc                                     26

<210> SEQ ID NO 4
<211> LENGTH: 26
<212> TYPE: RNA
<213> ORGANISM: Artificial Sequence
<220> FEATURE:
<223> OTHER INFORMATION: Synthetic construct

<400> SEQUENCE: 4
guucagaguu cuacagaccc auacga                                     26

<210> SEQ ID NO 5
<211> LENGTH: 32
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (20)..(25)
<223> OTHER INFORMATION: n is a, c, g, or u

<400> SEQUENCE: 5
guucagaguu cuacaguccn nnnnncauac ga                              32

<210> SEQ ID NO 6
<211> LENGTH: 21
<212> TYPE: DNA
<213> ORGANISM: Artificial Sequence
<220> FEATURE:
<223> OTHER INFORMATION: Synthetic construct

<400> SEQUENCE: 6

-continued caagcagaag acggcatacg a                                    21

<210> SEQ ID NO 7
<211> LENGTH: 31
<212> TYPE: DNA
<213> ORGANISM: Artificial Sequence
<220> FEATURE:
<223> OTHER INFORMATION: Synthetic construct

<400> SEQUENCE: 7
cctctctatg ggcagtcggt gatcaagcag a                         31

<210> SEQ ID NO 8
<211> LENGTH: 49
<212> TYPE: DNA
<213> ORGANISM: Artificial Sequence
<220> FEATURE:
<223> OTHER INFORMATION: Synthetic construct

<400> SEQUENCE: 8
ccatctcatc cctgcgtgtc tccgactcag gttcagagtt ctacagtcc      49

<210> SEQ ID NO 9
<211> LENGTH: 17
<212> TYPE: DNA
<213> ORGANISM: Artificial Sequence
<220> FEATURE:
<223> OTHER INFORMATION: Synthetic construct

<400> SEQUENCE: 9
cctctctatg ggcagtc                                         17

<210> SEQ ID NO 10
<211> LENGTH: 44
<212> TYPE: DNA
<213> ORGANISM: Artificial Sequence
<220> FEATURE:
<223> OTHER INFORMATION: Synthetic construct

<400> SEQUENCE: 10
uagcaccauu ugaaaucagu guutcgtatg ccgtcttctg cttg           44

<210> SEQ ID NO 11
<211> LENGTH: 43
<212> TYPE: DNA
<213> ORGANISM: Artificial Sequence
<220> FEATURE:
<223> OTHER INFORMATION: Synthetic construct

<400> SEQUENCE: 11
aagugccucc uuuuagagug uutcgtatgc cgtcttctgc ttg            43

<210> SEQ ID NO 12
<211> LENGTH: 43
<212> TYPE: DNA
<213> ORGANISM: Artificial Sequence
<220> FEATURE:
<223> OTHER INFORMATION: Synthetic construct

<400> SEQUENCE: 12
gcacugagau gggaguggug uatcgtatgc cgtcttctgc ttg            43

<210> SEQ ID NO 13
<211> LENGTH: 42
<212> TYPE: DNA

```
<213> ORGANISM: Artificial Sequence
<220> FEATURE:
<223> OTHER INFORMATION: Synthetic construct

<400> SEQUENCE: 13
gaagugugcc guguguguc utcgtatgcc gtcttctgct tg                          42
```